US012068729B2

(12) United States Patent
Chalothorn et al.

(10) Patent No.: US 12,068,729 B2
(45) Date of Patent: Aug. 20, 2024

(54) ANTI-FACTOR XII/XIIa ANTIBODIES AND USES THEREOF

(71) Applicant: Regeneron Pharmaceuticals, Inc., Tarrytown, NY (US)

(72) Inventors: Dan Chalothorn, New York, NY (US); Lori C. Morton, Chappaqua, NY (US); Lyndon Mitnaul, Piscataway, NJ (US); KehDih Lai, Yardley, PA (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 622 days.

(21) Appl. No.: 17/253,279

(22) PCT Filed: Jun. 19, 2019

(86) PCT No.: PCT/US2019/037865
§ 371 (c)(1),
(2) Date: Dec. 17, 2020

(87) PCT Pub. No.: WO2019/246176
PCT Pub. Date: Dec. 26, 2019

(65) Prior Publication Data
US 2021/0203292 A1 Jul. 1, 2021

Related U.S. Application Data

(60) Provisional application No. 62/687,144, filed on Jun. 19, 2018.

(51) Int. Cl.
*C07K 16/22* (2006.01)
*H03F 3/45* (2006.01)

(52) U.S. Cl.
CPC ........... *H03F 3/45475* (2013.01); *H03F 2203/45444* (2013.01)

(58) Field of Classification Search
CPC ........... H03F 3/45; C07K 16/22; A61K 39/00; A61P 11/00
USPC ........................................ 330/255, 252, 261
See application file for complete search history.

(56) References Cited

U.S. PATENT DOCUMENTS

| | | | |
|---|---|---|---|
| 4,963,657 A | 10/1990 | Pixley | |
| 5,500,349 A | 3/1996 | Esnouf | |
| 6,891,394 B1 * | 5/2005 | Yu | H03K 19/17784 326/38 |
| 7,378,867 B1 * | 5/2008 | Yu | H03K 19/017581 326/38 |
| 7,541,838 B2 * | 6/2009 | Tian | H03K 19/00369 330/252 |
| 8,119,137 B2 | 2/2012 | Nieswandt et al. | |
| 8,715,672 B2 | 5/2014 | Nieswandt et al. | |
| 9,518,127 B2 | 12/2016 | Panousis et al. | |
| 9,574,013 B2 | 2/2017 | Gruber et al. | |
| 9,856,325 B2 | 1/2018 | Panousis et al. | |
| 9,856,326 B2 | 1/2018 | Panousis et al. | |
| 11,405,242 B2 * | 8/2022 | Hossain | H04L 25/03057 |
| 2013/0095108 A1 | 4/2013 | Jablonska et al. | |
| 2014/0072572 A1 | 3/2014 | Nahrendorf et al. | |
| 2014/0072600 A1 | 3/2014 | Zeitler et al. | |
| 2015/0349728 A1 * | 12/2015 | Jeon | H03F 3/087 330/252 |

FOREIGN PATENT DOCUMENTS

| | | |
|---|---|---|
| EP | 1830924 B1 | 2/2013 |
| EP | 2623110 A1 | 8/2013 |
| WO | WO-1991017258 A1 | 11/1991 |
| WO | WO-2006066878 A1 | 6/2006 |
| WO | WO-2013014092 A1 | 1/2013 |
| WO | WO-2014089493 A1 | 6/2014 |

OTHER PUBLICATIONS

Pixley et al: "A Monoclonal Antibody Recognizing an Icosapeptide Sequence in the Heavy Chain of Human Factor XII Inhibits Surface-catalyzed Activation*", The Journal of Biological Chemistry, vol. 262, No. 21, Issue of Jul. 25, pp. 10140-10145, 1987.
Larsson et al, "A Factor XIIa Inhibitory Antibody Provides Thromboprotection in Extracorporeal Circulation Without Increasing Bleeding Risk," Sci Transl Med. Feb. 5, 2014;6(222).
Esnouf et al, "A Monoclonal Antibody Raised against Human ?-factor XIIa which also Recognizes ?- factor XIIa but not Factor XII or Complexes of Factor XIIa with C1 Esterase Inhibitor", Thhromb Haemost 2000; 83(06): 874-881.

* cited by examiner

*Primary Examiner* — Henry Choe
(74) *Attorney, Agent, or Firm* — McCarter & English, LLP; Marcie B. Clarke; Deborah L. Nagle

(57) ABSTRACT

The present invention provides monoclonal antibodies that bind to the Factor XII (FXII) protein, and methods of use thereof. In various embodiments of the invention, the antibodies are fully human antibodies that bind to FXII and to the activated form of FXII (FXIIa). In some embodiments, the antibodies of the invention are useful for inhibiting or neutralizing FXII activity, thus providing a means of treating or preventing a disease, disorder or condition associated with thrombosis in humans.

31 Claims, No Drawings

ANTI-FACTOR XII/XIIa ANTIBODIES AND USES THEREOF

RELATED APPLICATIONS

The present invention is a 35 U.S.C. § 371 national stage filing of International Application No. PCT/US2019/037865, filed on Jun. 19, 2019, which in turn claims the benefit of priority to U.S. Provisional Patent Application No. 62/687,144, filed on Jun. 19, 2018. The entire contents of each of the aforementioned applications are incorporated herein by reference.

SEQUENCE LISTING

The present application contains a Sequence Listing which has been submitted electronically in ASCII format and is hereby incorporated by reference in its entirety. Said ASCII copy, created on Jun. 18, 2019, is named 10463WO01_SL.txt and is 26,288 bytes in size.

FIELD OF THE INVENTION

The present invention is related to antibodies and antigen-binding fragments of antibodies that specifically bind to coagulation factor XII, and therapeutic and diagnostic methods of using those antibodies.

BACKGROUND OF THE INVENTION

Coagulation factors, along with platelets, are blood components relevant in the process of haemostasis during vessel injury. It is well-established that these components can be drivers of thrombosis when imbalances occur in regulation (i.e., production and/or activity). Thrombotic diseases were believed to primarily arise from aberrant activation in the extrinsic pathway (via tissue factor), but more recently, preclinical studies with F12 deficient mice and molecules that target activated FXII (FXIIa) suggested that the intrinsic pathway (also known as the contact pathway) of coagulation is also involved (Renne et al 2005, J. Exp. Med. 202: 271-81; Larsson et al 2014, Sci. Transl. Med. 6: 222ra17). FXIIa is central to the contact pathway and can drive coagulation via cleavage of FXI or can drive inflammation via cleavage of plasma prekallikrein. Thus, inhibition of FXII activity may lead to reduced thrombotic coagulation and inflammation associated with contact pathway activation (Schousboe 2007, Biochem. Pharmacol. 75: 1007-13; Danese et al 2016, Semin. Thromb. Hemostat. 42: 682-8; Weitz 2016, Thromb. Res. 141 Suppl. 2: S40-5). The anticoagulants used presently in the art, e.g., heparin, are effective anti-thrombotics yet they also increase the risk for bleeding. Thus, it is desirable to develop anti-coagulants that prevent thrombosis without increasing the risk of bleeding.

Monoclonal antibodies to FXII are known in the art and have been described, for example, in US Patent/Publication Nos. 4963657, 5500349, 8119137, 8715672, 9856326, 9856325, 9518127, 20130095108, 20140072572, 20140072600, and in WO2006066878, WO2013014092, EP1830924B1, EP27345522A1, and EP2623110A1.

Fully human antibodies that specifically bind to (activated) FXII protein with high affinity and prevent thrombosis without increasing the risk of bleeding could be important in the prevention and treatment of various FXII-associated diseases (e.g., thrombosis, embolism, edema).

BRIEF SUMMARY OF THE INVENTION

The present invention provides antibodies and antigen-binding fragments thereof that specifically bind the activated form of coagulation Factor XII protein (FXIIa). In certain embodiments, the antibodies also bind the zymogen form of Factor XII (FXII). In certain embodiments, the antibodies are fully human antibodies that bind to FXII and also to FXIIa ("dual FXII/FXIIa binders") with high affinity. The antibodies of the present invention are useful, inter alia, for inhibiting or neutralizing the activity of FXII protein. In certain embodiments, the antibodies are useful in preventing, treating or ameliorating at least one symptom or indication of a FXII-associated disease or disorder in a subject. In certain embodiments, the antibodies may be administered prophylactically or therapeutically to a subject having or at risk of having a FXII-associated disease or disorder. In certain preferred embodiments. In specific embodiments, the antibodies prevent thrombosis without increasing bleeding risk in a subject. Such antibodies can be used as anticoagulation therapy without increasing risk of bleeding when administered to a subject in need thereof, along with less frequent dosing in a subject with a FXII-associated disease or disorder.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to Factor XII (FXII) and/or activated Factor XII (FXIIa). In some embodiments, the antibodies are fully human monoclonal antibodies. In certain embodiments, the antibodies are "dual binders," being able to bind FXII and FXIIa.

Exemplary anti-FXII/FXIIa antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDRs) (HCDR1, HCDR2 and HCDR3), and light chain complementarity determining regions (LCDRs) (LCDR1, LCDR2 and LCDR3) of exemplary antibodies. Table 2 sets forth the nucleic acid sequence identifiers of the HCVRs, LCVRs, HCDR1, HCDR2 HCDR3, LCDR1, LCDR2 and LCDR3 of the exemplary antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-FXII/FXIIa antibodies listed in Table 1. In certain embodiments, the HCVR/LCVR amino acid sequence pair is selected from one of SEQ ID NOs: 2/10 (e.g., mAb26036), 18/26 (e.g., mAb26048), 34/42 (e.g., mAb26049), or 50/58 (e.g., mAb26076).

The present invention also provides antibodies, or antigen-binding fragments thereof, comprising a HCVR and a LCVR, said HCVR comprising an amino acid sequence listed in Table 1 having no more than twelve amino acid substitutions, and/or said LCVR comprising an amino acid sequence listed in Table 1 having no more than ten amino acid substitutions. For example, the present invention provides antibodies or antigen-binding fragments thereof comprising a HCVR and a LCVR, said HCVR comprising an amino acid sequence selected from the group consisting of SEQ ID NOs: 2, 18, 34, and 50, said amino acid sequence having one, two, three, four, five, six, seven, eight, nine, ten, eleven or twelve amino acid substitutions. In another example, the present invention provides antibodies or antigen-binding fragments thereof comprising a HCVR and a LCVR, said LCVR comprising an amino acid sequence selected from the group consisting of SEQ ID NOs: 10, 26, 42, and 58, said amino acid sequence having one, two, three, four, five, six, seven, eight, nine or ten amino acid substitutions. In one embodiment, the present invention provides anti-FXII/FXIIa antibodies or antigen-binding fragments thereof comprising a HCVR and a LCVR, said HCVR comprising an amino acid sequence selected from the group consisting of SEQ ID NOs: 2, 18, 34, and 50, said amino acid sequence having at least one amino acid substitution, and/or said LCVR comprising an amino acid sequence selected from the group consisting of SEQ ID NO: 10, 26, 42, and 58, said amino acid sequence having at least one amino acid substitution.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-FXII antibodies listed in Table 1. In certain embodiments, the HCDR3/LCDR3 amino acid sequence pair is selected from the group consisting of SEQ ID NOs: 8/16 (e.g., mAb26036), 24/32 (e.g., mAb26048), 40/48 (e.g., mAb26049), and 56/64 (e.g., mAb26076).

The present invention also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides antibodies, or antigen-binding fragments thereof, comprising a HCVR and a LCVR, said HCVR comprising HCDR1 comprising an amino acid sequence of SEQ ID NO: 4 or an amino acid sequence differing from SEQ ID NO: 4 by 1 amino acid, HCDR2 comprising an amino acid sequence of SEQ ID NO: 6 or an amino acid sequence differing from SEQ ID NO: 6 by 1 amino acid, and HCDR3 comprising an amino acid sequence of SEQ ID NO: 8 or an amino acid sequence differing from SEQ ID NO: 8 by 1 amino acid. In another exemplary embodiment, the present invention provides antibodies, or antigen-binding fragments thereof, comprising a HCVR and a LCVR, said LCVR comprising LCDR1 comprising an amino acid sequence of SEQ ID NO: 12 or an amino acid sequence differing from SEQ ID NO: 12 by 1 amino acid, LCDR2 comprising an amino acid sequence of SEQ ID NO: 14 or an amino acid sequence differing from SEQ ID NO: 14 by 1 amino acid, and LCDR3 comprising an amino acid sequence of SEQ ID NO: 16 or an amino acid sequence differing from SEQ ID NO: 16 by 1 amino acid.

The present invention also provides antibodies, or antigen-binding fragments thereof, comprising a set of six CDRs (i.e., HCDR1-HCDR2-HCDR3-LCDR1-LCDR2-LCDR3) contained within any of the exemplary antibodies listed in Table 1. In certain embodiments, the HCDR1-

HCDR2-HCDR3-LCDR1-LCDR2-LCDR3 amino acid sequence set is selected from the group consisting of SEQ ID NOs: 4-6-8-12-14-16 (e.g., mAb26036), 20-22-24-28-30-32 (e.g., mAb26048), 36-38-40-44-46-48 (e.g., mAb26049), and 52-54-56-60-62-64 (e.g., mAb26076).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., mAb26036), 18/26 (e.g., mAb26048), 34/42 (e.g., mAb26049), or 50/58 (e.g., mAb26076). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments, the present invention includes an antibody or antigen-binding fragment thereof that binds specifically to FXII and/or FXIIa, wherein the antibody or antigen-binding fragment thereof comprises three heavy chain complementarity determining regions (CDRs) (HCDR1, HCDR2 and HCDR3) contained within a heavy chain variable region (HCVR) and three light chain CDRs (LCDR1, LCDR2 and LCDR3) contained within a light chain variable region (LCVR), wherein the HCVR comprises: (i) the amino acid sequence selected from the group consisting of SEQ ID NOs: 2, 18, 34, and 50, (ii) an amino acid sequence having at least 90% identity to an amino acid sequence selected from the group consisting of SEQ ID NOs: 2, 18, 34, and 50, (iii) an amino acid sequence having at least 95% identity to an amino acid sequence selected from the group consisting of SEQ ID NOs: 2, 18, 34, and 50; or (iv) the amino acid sequence selected from the group consisting of SEQ ID NOs: 2, 18, 34, and 50 having no more than 12 amino acid substitutions; and the LCVR comprises: (i) the amino acid sequence selected from the group consisting of SEQ ID NOs: 10, 26, 42, and 58, (ii) an amino acid sequence having at least 90% identity to an amino acid sequence selected from the group consisting of SEQ ID NOs: 10, 26, 42, and 58, (iii) an amino acid sequence having at least 95% identity to an amino acid sequence selected from the group consisting of SEQ ID NOs: 10, 26, 42, and 58; or (iv) the amino acid sequence selected from the group consisting of SEQ ID NOs: 10, 26, 42, and 58 having no more than 10 amino acid substitutions.

The present invention includes anti-FXII/FXIIa antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In certain embodiments, the present invention provides antibodies and antigen-binding fragments thereof that exhibit pH-dependent binding to FXII. For example, the present invention includes antibodies and antigen-binding fragment thereof that bind FXII with higher affinity at neutral pH than at acidic pH (i.e., reduced binding at acidic pH).

The present invention also provides for antibodies and antigen-binding fragments thereof that compete for specific binding to FXII or to FXIIa with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that cross-compete for binding to FXII/FXIIa with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that bind to the same epitope as a reference antibody or antigen-binding fragment thereof comprising three CDRs of a HCVR and three CDRs of a LCVR, wherein the HCVR and LCVR each has an amino acid sequence selected from the HCVR and LCVR sequences listed in Table 1.

In some embodiments, the antibody or antigen binding fragment thereof may bind specifically to FXII and/or FXIIa in an agonist manner, i.e., it may enhance or stimulate FXII/FXIIa binding and/or activity; in other embodiments, the antibody may bind specifically to FXII and/or FXIIa in an antagonist manner, i.e., it may block FXII binding and/or activity.

The present invention also provides isolated antibodies and antigen-binding fragments thereof that block FXIIa binding to FXI. In some embodiments, the antibody or antigen-binding fragment thereof that blocks FXIIa binding to FXI may bind to the same epitope on FXIIa as FXI or may bind to a different epitope on FXIIa as FXI.

In certain embodiments, the antibodies or antigen-binding fragments of the present invention are bispecific comprising a first binding specificity to a first epitope of FXII/FXIIa and a second binding specificity to a second epitope of FXII/FXIIa wherein the first and second epitopes are distinct and non-overlapping.

In certain embodiments, the present invention provides an isolated antibody or antigen-binding fragment thereof that has one or more of the following characteristics: (a) is a fully human monoclonal antibody; (b) binds to activated Factor XII (FXIIa); (c) binds to FXII with a dissociation constant ($K_D$) of less than 3.5 nM at 25° C., as measured in a surface plasmon resonance assay; (d) binds to FXII with a $K_D$ of less than 17 nM at 37° C., as measured in a surface plasmon resonance assay; (e) binds to FXIIa with a $K_D$ of less than 5 nM, preferably less than 2.5 nM, at 25° C. as measured in a surface plasmon resonance assay; (f) binds to FXIIa with a $K_D$ of less than 6.5 nM, preferably less than 2.5 nM, at 37° C. as measured in a surface plasmon resonance assay; (g) blocks thrombin generation by intrinsic pathway at a concentration of less than 250 nM, as measured by functional plasma assays; and (h) blocks thrombin generation by intrinsic pathway without blocking thrombin generation by extrinsic pathway, as measured by functional plasma assays.

In a second aspect, the present invention provides nucleic acid molecules encoding anti-FXII/FXIIa antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-FXII antibody listed in Table 1.

In a related aspect, the present invention provides recombinant expression vectors capable of expressing a polypeptide comprising a heavy or light chain variable region of an antibody. For example, the present invention includes recombinant expression vectors comprising any of the nucleic acid molecules mentioned above, i.e., nucleic acid molecules encoding any of the HCVR, LCVR, and/or CDR sequences as set forth in Table 2. In certain embodiments, the present invention provides expression vectors comprising: (a) a nucleic acid molecule comprising a nucleic acid sequence encoding a HCVR of an antibody that binds FXII/FXIIa, wherein the HCVR comprises an amino acid sequence selected from the group consisting of sequences listed in Table 1; and/or (b) a nucleic acid molecule comprising a nucleic acid sequence encoding a LCVR of an antibody that binds FXII/FXIIa, wherein the LCVR comprises an amino acid sequence selected from the group consisting of sequences listed in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced. In certain embodiments, the host cells comprise a mammalian cell or a prokaryotic cell. In certain embodiments, the host cell is a Chinese Hamster Ovary (CHO) cell or an *Escherichia coli* (*E. coli*) cell. In certain embodiments, the present invention provides methods of producing an antibody or antigen-binding fragment thereof of the invention, the methods comprising introducing into a host cell an expression vector comprising a nucleic acid sequence encoding a HCVR and/or LCVR of an antibody or antigen-binding fragment thereof operably linked to a promoter; culturing the host cell under conditions favorable for expression of the nucleic acid sequence; and isolating the antibody or antigen-binding fragment thereof from the culture medium and/or host cell. The isolated antibody or antigen-binding fragment thereof may purified using any of the methods known in prior art.

In a third aspect, the invention provides a pharmaceutical composition comprising a therapeutically effective amount of at least one recombinant monoclonal antibody or antigen-binding fragment thereof which specifically binds FXII/FXIIa and a pharmaceutically acceptable carrier. In a related aspect, the invention features a composition which is a combination of an anti-FXII/FXIIa antibody and a second therapeutic agent. In one embodiment, the second therapeutic agent is any agent that is advantageously combined with an anti-FXII/FXIIa antibody. Exemplary agents that may be advantageously combined with an anti-FXII/FXIIa antibody include, without limitation, other agents that bind and/or inhibit FXII activity (including other antibodies or antigen-binding fragments thereof, etc.) and/or agents which do not directly bind FXII but nonetheless treat or ameliorate at least one symptom or indication of a FXII-associated disease or disorder. Additional combination therapies and co-formulations involving the anti-FXII antibodies of the present invention are disclosed elsewhere herein.

In a fourth aspect, the invention provides therapeutic methods for treating a disease or disorder associated with FXII in a subject using an anti-FXII/FXIIa antibody or antigen-binding portion of an antibody of the invention, wherein the therapeutic methods comprise administering a therapeutically effective amount of a pharmaceutical composition comprising an antibody or antigen-binding fragment of an antibody of the invention to the subject in need thereof. The disorder treated is any disease or condition which is improved, ameliorated, inhibited or prevented by inhibition of FXII activity. In certain embodiments, the invention provides methods to prevent, or treat a FXII-associated disease or disorder comprising administering a therapeutically effective amount of an anti-FXII/FXIIa antibody or antigen-binding fragment thereof of the invention to a subject in need thereof. In some embodiments, the antibody or antigen-binding fragment thereof may be administered prophylactically or therapeutically to a subject having or at risk of having a FXII-associated disease or disorder. In certain embodiments, the antibody or antigen-binding fragment thereof the invention is administered in combination with a second therapeutic agent to the subject in need thereof. The second therapeutic agent may be selected from the group consisting of an anti-coagulant, a direct thrombin inhibitor, a thrombolytic drug, a fibrinolytic drug, an anti-platelet drug, an anti-inflammatory drug, an anti-hypertensive drug, a second anti-FXII antibody, a lipid-lowering drug, mechanical clot retrieval, catheter-guided thrombolysis, compression stockings, surgery and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, or intramuscularly. The antibody or fragment thereof may be administered at a dose of about 0.1 mg/kg of body weight to about 100 mg/kg of body weight of the subject. In certain embodiments, an antibody of the present invention may be administered at one or more doses comprising between 10 mg to 600 mg.

The present invention also includes use of an anti-FXII/FXIIa antibody or antigen-binding fragment thereof of the invention in the manufacture of a medicament for the treatment of a disease or disorder that would benefit from the blockade of FXII/FXIIa binding and/or activity.

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "FXII", also called "Factor XII" refers to coagulation Factor XII, also known as Hageman Factor. The 596-amino acid FXII protein is the zymogen form of Factor XIIa, a beta-globulin plasma serine protease composed of an amino-terminal heavy chain and a carboxy-terminal light chain. Its heavy chain contains two fibronectin-type domains (type I and II), two epidermal growth factor-like domains, a Kringle domain, and a proline-rich region, and its light chain contains the protease domain. Exposure of blood to negatively charged substances or artificial surfaces triggers thrombin generation and fibrin formation via a series of reactions known as contact activation. Factor XII activates Factor XI and prekallikrein in the coagulation cascade. Factor XII itself is activated to Factor XIIa by plasma kallikrein, platelet or bacterial polyphosphates, extracellular DNA or RNA, heparins released from mast cells, amyloid peptides, misfolded protein aggregates and negatively charged surfaces, such as glass. This is the starting point of the intrinsic pathway. The amino acid sequence of full-length FXII protein is exemplified by the amino acid sequence provided in UniProtKB/Swiss-Prot as accession number P00748.3. The amino acid sequence of full-length FXII protein is also shown as SEQ ID NO: 65 herein. The term "FXII" includes recombinant FXII protein or a fragment thereof. The term also encompasses FXII protein or a fragment thereof coupled to, for example, histidine tag, mouse or human Fc, or a signal sequence such as ROR1.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-FXII monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-FXII monoclonal antibodies comprising variants of any of the HCVR, LCVR, and/or CDR amino acid sequences disclosed herein having one or more conservative substitutions. For example, the present invention includes anti-FXII antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to FXII. Moreover, multi-specific antibodies that bind to one domain in FXII and one or more additional antigens or a bi-specific that binds to two different regions of FXII are nonetheless considered antibodies that "specifically bind", as used herein.

The term "high affinity" antibody refers to those mAbs having a binding affinity to FXII, expressed as $K_D$, of at least $10^{-8}$ M; preferably $10^{-9}$ M; more preferably $10^{-10}$ M, even more preferably $10^{-11}$ M, as measured by surface plasmon resonance, e.g., BIACORE™ or solution-affinity ELISA.

By the term "slow off rate", "Koff" or "kd" is meant an antibody that dissociates from FXII, with a rate constant of $1×10^{-3}$ $s^{-1}$ or less, preferably $1×10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to FXII protein.

In specific embodiments, antibody or antibody fragments of the invention may be conjugated to a moiety such a ligand or a therapeutic moiety ("immunoconjugate"), a second anti-FXII antibody, or any other therapeutic moiety useful for treating a FXII-associated disease or disorder.

An "isolated antibody", as used herein, is intended to refer to an antibody that is substantially free of other antibodies (Abs) having different antigenic specificities (e.g., an isolated antibody that specifically binds FXII and/or FXIIa, or a fragment thereof, is substantially free of Abs that specifically bind antigens other than FXII or FXIIa.

A "blocking antibody" or a "neutralizing antibody", as used herein (or an "antibody that neutralizes FXII activity" or "antagonist antibody"), is intended to refer to an antibody whose binding to FXII/FXIIa results in inhibition of at least one biological activity of FXII. For example, an antibody of the invention may prevent or block coagulation by the intrinsic pathway.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains:

aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a FXII-associated disease or disorder such as thrombosis or embolism. The term includes human subjects who have or are at risk of having such a disease or disorder.

As used herein, the terms "treat", "treating", or "treatment" refer to the reduction or amelioration of the severity of at least one symptom or indication of a FXII-associated disease or disorder due to the administration of a therapeutic agent such as an antibody of the present invention to a subject in need thereof. The terms include inhibition of progression of disease or of worsening of a symptom/indication. The terms also include positive prognosis of disease, i.e., the subject may be free of disease or may have reduced disease upon administration of a therapeutic agent such as an antibody of the present invention. The therapeutic agent may be administered at a therapeutic dose to the subject.

The terms "prevent", "preventing" or "prevention" refer to inhibition of manifestation of a FXII-associated disease or disorder or any symptoms or indications of such a disease or disorder upon administration of an antibody of the present invention.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to FXII protein. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multispecific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v)

$V_H$-$C_H1$-$C_H2$-$C_H3$; (vi) $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to FXII and/or FXIIa.

An immunogen comprising any one of the following can be used to generate antibodies to FXII and/or FXIIa protein. In certain embodiments, the antibodies of the invention are obtained from mice immunized with a full length, native FXII or FXIIa protein (See, for example, UniProtKB/Swiss-Prot accession number P00748.3) or with DNA encoding the protein or fragment thereof. Alternatively, the protein or a fragment thereof may be produced using standard biochemical techniques and modified and used as immunogen.

In some embodiments, the immunogen may be a recombinant FXII protein or fragment thereof expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to FXII are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-FXII antibodies and antibody fragments of the present invention encompass proteins having amino acid sequences that vary from those of the described antibodies, but that retain the ability to bind FXII protein. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-FXII Antibodies Comprising Fc Variants

According to certain embodiments of the present invention, anti-FXII antibodies are provided comprising an Fc domain comprising one or more mutations which enhance or diminish antibody binding to the FcRn receptor, e.g., at acidic pH as compared to neutral pH. For example, the present invention includes anti-FXII antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-FXII antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311 I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present invention.

The present invention also includes anti-FXII antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Patent Application Publication 2014/0243504, the disclosure of which is hereby incorporated by reference in its entirety).

Biological Characteristics of the Antibodies

In general, the antibodies of the present invention function by binding to FXII protein and preventing its cleavage to FXIIa and FXIIb. In certain embodiments, the antibodies bind to the activated form of Factor XII (FXIIa) ("dual FXII/FXIIa binders"). For example, the present invention includes antibodies and antigen-binding fragments of antibodies that bind FXII protein (e.g., at 25° C. or at 37° C.) with a $K_D$ of less than 20 nM as measured by surface plasmon resonance, e.g., using the assay format as defined in Example 3 herein. In certain embodiments, the antibodies or antigen-binding fragments thereof bind FXII with a $K_D$ of less than about 20 nM, less than about 17 nM, less than about 10 nM, less than about 5 nM, or less than about 1 nM, as measured by surface plasmon resonance, e.g., using the assay format as defined in Example 3 herein, or a substantially similar assay.

The present invention also includes antibodies and antigen-binding fragments thereof that bind human FXII protein with a dissociative half-life (t½) of greater than about 1 minute as measured by surface plasmon resonance at 25° C. or at 37° C., e.g., using an assay format as defined in Example 3 herein, or a substantially similar assay. In certain embodiments, the antibodies or antigen-binding fragments of the present invention bind FXII protein with a t½ of greater than about 5 minutes, greater than about 10 minutes, greater than about 20 minutes, greater than about 30 minutes, greater than about 40 minutes, greater than about 50 minutes, greater than about 60 minutes, or greater than about 70 minutes, as measured by surface plasmon resonance at 25° C. or at 37° C., e.g., using an assay format as defined in Example 3 herein, or a substantially similar assay.

The present invention includes antibodies and antigen-binding fragments of antibodies that bind FXIIa protein (e.g., at 25° C. or at 37° C.) with a $K_D$ of less than 9 nM as measured by surface plasmon resonance, e.g., using the assay format as defined in Example 3 herein. In certain embodiments, the antibodies or antigen-binding fragments thereof bind FXIIa with a $K_D$ of less than about 9 nM, less than about 5 nM, less than about 2 nM, less than about 1 nM, or less than about 500 pM, as measured by surface plasmon resonance, e.g., using the assay format as defined in Example 3 herein, or a substantially similar assay.

The present invention also includes antibodies and antigen-binding fragments thereof that bind human FXIIa protein with a dissociative half-life (t½) of greater than about 1 minute as measured by surface plasmon resonance at 25° C. or at 37° C., e.g., using an assay format as defined in Example 3 herein, or a substantially similar assay. In certain embodiments, the antibodies or antigen-binding fragments of the present invention bind FXIIa protein with a t½ of greater than about 5 minutes, greater than about 10 minutes, greater than about 20 minutes, greater than about 30 minutes, greater than about 40 minutes, greater than about 50 minutes, greater than about 60 minutes, or greater than about 70 minutes, as measured by surface plasmon resonance at 25° C. or at 37° C., e.g., using an assay format as defined in Example 3 herein, or a substantially similar assay.

The present invention also includes antibodies and antigen-binding fragments thereof that inhibit thrombin generation by intrinsic pathway at a concentration of less than 250 nM, less than 200 nM or less than 150 nM, as measured, e.g., using an assay format as described in Example 5 herein, or a substantially similar assay. In certain embodiments, the present invention includes antibodies and antigen-binding fragments thereof that inhibit thrombin generation by intrinsic pathway without blocking thrombin generation by extrinsic pathway, as measured, e.g., using an assay format as described in Example 5 herein, or a substantially similar assay.

In one embodiment, the present invention provides an isolated recombinant antibody or antigen-binding fragment thereof that binds specifically to FXII protein, wherein the antibody or fragment thereof exhibits one or more of the following characteristics: (a) is a fully human monoclonal antibody; (b) binds to activated Factor XII (FXIIa); (c) binds to FXII with a dissociation constant ($K_D$) of less than 3.5 nM at 25° C., as measured in a surface plasmon resonance assay; (d) binds to FXII with a $K_D$ of less than 17 nM at 37° C., as measured in a surface plasmon resonance assay; (e) binds to FXIIa with a $K_D$ of less than 5 nM, preferably less than 2.5 nM, at 25° C. as measured in a surface plasmon resonance assay; (f) binds to FXIIa with a $K_D$ of less than 6.5 nM, preferably less than 2.5 nM, at 37° C. as measured in a surface plasmon resonance assay; (g) blocks thrombin generation by intrinsic pathway at a concentration of less than 250 nM, as measured by functional plasma assays; and (h) blocks thrombin generation by intrinsic pathway without blocking thrombin generation by extrinsic pathway, as measured by functional plasma assays.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Epitope Mapping and Related Technologies

The present invention includes anti-FXII/FXIIa antibodies which interact with one or more amino acids found within one or more regions of the FXII/FXIIa protein molecule including, the heavy chain and the light chain. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the FXII protein molecule (e.g. a linear epitope in a domain). Alternatively, the epitope may consist of a plurality of non-contiguous amino acids (or amino acid sequences) located within either or both of the aforementioned domains of the protein molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the present invention includes anti-FXII antibodies and antigen-binding fragments thereof that interact with one or more epitopes found within the heavy and/or light chain of FXIIa. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within heavy chain and/or light chain of FXIIa. Alternatively, the epitope may consist of a plurality of non-contiguous amino acids (or amino acid sequences) located within FXIIa.

The present invention includes anti-FXII antibodies that bind to the same epitope, or a portion of the epitope, as any of the specific exemplary antibodies listed in Table 1. Likewise, the present invention also includes anti-FXII antibodies that compete for binding to FXII protein or a fragment thereof with any of the specific exemplary antibodies listed in Table 1. For example, the present invention includes anti-FXII antibodies that cross-compete for binding to FXII protein with one or more antibodies listed in Table 1.

One can easily determine whether an antibody binds to the same epitope as, or competes for binding with, a reference anti-FXII antibody by using routine methods known in the art. For example, to determine if a test antibody binds to the same epitope as a reference anti-FXII antibody of the invention, the reference antibody is allowed to bind to a FXII protein or peptide under saturating conditions. Next, the ability of a test antibody to bind to the FXII protein molecule is assessed. If the test antibody is able to bind to FXII following saturation binding with the reference anti-FXII antibody, it can be concluded that the test antibody binds to a different epitope than the reference anti-FXII antibody. On the other hand, if the test antibody is not able to bind to the FXII protein following saturation binding with the reference anti-FXII antibody, then the test antibody may bind to the same epitope as the epitope bound by the reference anti-FXII antibody of the invention.

To determine if an antibody competes for binding with a reference anti-FXII antibody, the above-described binding methodology is performed in two orientations: In a first orientation, the reference antibody is allowed to bind to a FXII protein under saturating conditions followed by assessment of binding of the test antibody to the FXII molecule. In a second orientation, the test antibody is allowed to bind to a FXII molecule under saturating conditions followed by assessment of binding of the reference antibody to the FXII molecule. If, in both orientations, only the first (saturating) antibody is capable of binding to the FXII molecule, then it is concluded that the test antibody and the reference antibody compete for binding to FXII. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-FXII monoclonal antibody conjugated to a therapeutic moiety ("immunoconjugate"), to treat a FXII-associated disease or disorder (e.g., thrombosis). As used herein, the term "immunoconjugate" refers to an antibody which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to FXII protein. The type of therapeutic moiety that may be conjugated to the anti-FXII antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, FXII-specific antibodies are generated in a bi-specific format (a "bi-specific") in which variable regions binding to distinct domains of FXII protein are linked together to confer dual-domain specificity within a single binding molecule. Appropriately designed bi-specifics may enhance overall FXII-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-FXII antibody, may be prepared in a bi-specific format using techniques described herein, or other techniques known to those skilled in the art. Antibody variable regions binding to distinct regions may be linked together with variable regions that bind to relevant sites on, for example, the extracellular domain of FXII, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-FXII antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 100 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 600 mg, about 5 to about 500 mg, or about 10 to about 400 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target cells.

Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracranial, intraperitoneal and intramuscular injections, drip infusions, etc. These injectable preparations may be prepared by methods publicly known.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

Therapeutic Uses of the Antibodies

The antibodies of the present invention are useful for the treatment, and/or prevention of a disease or disorder or condition associated with coagulation (including thrombosis and embolism) or edema (e.g., hereditary angioedema) and/or for ameliorating at least one symptom associated with such disease, disorder or condition. In certain embodiments, an antibody or antigen-binding fragment thereof of the invention may be administered at a therapeutic dose to a patient with a disease or disorder or condition associated with coagulation or with edema. In certain embodiments, an antibody or antigen-binding fragment thereof of the invention is administered to a subject in need thereof to prevent thrombosis without increasing risk of bleeding.

In certain embodiments, the antibodies of the present invention are useful for treating or preventing at least one symptom or indication of a FXII-associated disease or disorder selected from the group consisting of venous thrombosis, arterial thrombosis, device thrombosis, thromboembolism, hereditary angioedema, stroke, thrombophilia, cardiac ischemia, atherosclerotic plaque rupture, use of mechanical valve prostheses, use of blood-contacting medical devices, use of blood-contacting extracorporeal circuits, venous thromboembolism, pulmonary embolism, deep vein thrombosis, portal vein thrombosis, Budd-Chiari syndrome, Paget-Schroetter disease, renal vein thrombosis, cerebral venous sinus thrombosis, jugular vein thrombosis, cavernous sinus thrombosis, hepatic artery thrombosis, limb ischemia and myocardial infarction.

It is also contemplated herein to use one or more antibodies of the present invention prophylactically to subjects at risk for thrombosis such as subjects using extracorporeal membrane oxygenation (heart-lung machine). An antibody of the invention may be used to prevent thrombotic occlusions of the oxygenator and tubing in the extracorporeal circuit.

In a further embodiment of the invention, the present antibodies are used for the preparation of a pharmaceutical composition or medicament for treating patients suffering from a disease, disorder or condition disclosed herein. In another embodiment of the invention, the present antibodies are used as adjunct therapy with any other agent or any other therapy known to those skilled in the art useful for treating or ameliorating a disease, disorder or condition disclosed herein.

Combination Therapies

Combination therapies may include an antibody of the invention and any additional therapeutic agent that may be advantageously combined with an antibody of the invention, or with a biologically active fragment of an antibody of the invention. The antibodies of the present invention may be combined synergistically with one or more drugs or therapy used to treat a disease or disorder associated with thrombosis, specifically to prevent thrombosis or to treat a subject at risk of thrombosis due to an underlying disease, disorder or condition (described elsewhere herein). In some embodiments, the antibodies of the invention may be combined with a second therapeutic agent to ameliorate one or more symptoms of said disease or condition.

Depending upon the disease, disorder or condition, the antibodies of the present invention may be used in combination with one or more additional therapeutic agents including, but not limited to, an anti-coagulant (e.g., warfarin, heparin, phenindione, fondaparinux, idraparinux), a thrombin inhibitor (e.g., argatroban, lepirudin, bivalirudin, or dabigatran), a thrombolytic drug, an anti-platelet drug (e.g., aspirin), an antihypertensive (e.g., an angiotensin-converting enzyme inhibitor, a beta blocker, a calcium channel blocker), an immunosuppressive agent (e.g., vincristine, cyclosporine A, or methotrexate), a fibrinolytic agent, a cholesterol-lowering agent (e.g., a statin or a PCSK9 inhibitor such as alirocumab), an anti-inflammatory drug (e.g., a corticosteroid, or a non-steroidal anti-inflammatory drug), a second anti-FXII antibody, mechanical clot retrieval, catheter-guided thrombolysis and surgery.

As used herein, the term "in combination with" means that additional therapeutically active component(s) may be administered prior to, concurrent with, or after the administration of the anti-FXII antibody of the present invention. The term "in combination with" also includes sequential or concomitant administration of an anti-FXII antibody and a second therapeutic agent.

The additional therapeutically active component(s) may be administered to a subject prior to administration of an anti-FXII antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, or less than 30 minutes before administration of the second component. In other embodiments, the additional therapeutically active component(s) may be administered to a subject after administration of an anti-FXII antibody of the present invention. For example, a first component may be deemed to be administered "after" a second component if the first component is administered 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after or more after administration of the second component. In yet other embodiments, the additional therapeutically active component(s) may be administered to a subject concurrent with administration of an anti-FXII antibody of the present invention. "Concurrent" administration, for purposes of the present invention, includes, e.g., administration of an anti-FXII antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-FXII antibody and the additional therapeutically active component may be administered intravenously, etc.); alternatively, each dosage form may be administered via a different route (e.g., the anti-FXII antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-FXII antibody "prior to", "concurrent with," or "after" (as those terms are defined herein above) administration of an additional therapeutically active component is considered administration of an anti-FXII antibody "in combination with" an additional therapeutically active component.

The present invention includes pharmaceutical compositions in which an anti-FXII antibody of the present invention is co-formulated with one or more of the additional therapeutically active component(s) as described elsewhere herein.

Diagnostic Uses of the Antibodies

The antibodies of the present invention may be used to detect and/or measure FXII in a sample, e.g., for diagnostic purposes. Some embodiments contemplate the use of one or more antibodies of the present invention in assays to detect a FXII-associated-disease or disorder. Exemplary diagnostic assays for FXII may comprise, e.g., contacting a sample, obtained from a patient, with an anti-FXII antibody of the invention, wherein the anti-FXII antibody is labeled with a detectable label or reporter molecule or used as a capture ligand to selectively isolate FXII from patient samples. Alternatively, an unlabeled anti-FXII antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, ß-galactosidase, horseradish peroxidase, or luciferase. Specific exemplary assays that can be used to detect or measure FXII in a sample include enzyme-linked immunosorbent assay (ELISA), radioimmunoassay (RIA), and fluorescence-activated cell sorting (FACS).

Samples that can be used in FXII diagnostic assays according to the present invention include any tissue or fluid sample obtainable from a patient, which contains detectable quantities of either FXII protein, or fragments thereof, under normal or pathological conditions. Generally, levels of FXII protein in a particular sample obtained from a healthy patient (e.g., a patient not afflicted with a disease associated with FXII) will be measured to initially establish a baseline, or standard, level of FXII. This baseline level of FXII can then be compared against the levels of FXII measured in samples obtained from individuals suspected of having a FXII-associated condition, or symptoms associated with such condition.

The antibodies specific for FXII protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Factor XII/Activated Factor XII (FXII/FXIIa) Proteins Human antibodies to FXII/FXIIa proteins were generated in a VELOCIMMUNE® mouse comprising DNA encoding human Immunoglobulin heavy and kappa light chain variable regions. The mice were immunized with plasma purified human FXII and FXIIa proteins (Enzyme Research Laboratories).

Anti-FXII antibodies were isolated directly from antigen-positive mouse B cells without fusion to myeloma cells, as described in U.S. Pat. No. 7,582,298, herein specifically incorporated by reference in its entirety. Using this method, several fully human anti-FXII antibodies (i.e., antibodies possessing human variable domains and human constant domains) were obtained; exemplary antibodies generated in this manner were designated as mAb26036, mAb26048, mAb26049, and mAb26076.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-FXII antibodies of the invention.

TABLE 1

Amino Acid Sequence Identifiers

| Antibody Designation | SEQ ID NOS: | | | | | | | |
|---|---|---|---|---|---|---|---|---|
| | HCVR | HCDR1 | HCDR2 | HCDR3 | LCVR | LCDR1 | LCDR2 | LCDR3 |
| mAb26036 | 2 | 4 | 6 | 8 | 10 | 12 | 14 | 16 |
| mAb26048 | 18 | 20 | 22 | 24 | 26 | 28 | 30 | 32 |
| mAb26049 | 34 | 36 | 38 | 40 | 42 | 44 | 46 | 48 |
| mAb26076 | 50 | 52 | 54 | 56 | 58 | 60 | 62 | 64 |

The corresponding nucleic acid sequence identifiers are set forth in Table 2.

TABLE 2

Nucleic Acid Sequence Identifiers

| Antibody Designation | SEQ ID NOS: | | | | | | | |
|---|---|---|---|---|---|---|---|---|
| | HCVR | HCDR1 | HCDR2 | HCDR3 | LCVR | LCDR1 | LCDR2 | LCDR3 |
| mAb26036 | 1 | 3 | 5 | 7 | 9 | 11 | 13 | 15 |
| mAb26048 | 17 | 19 | 21 | 23 | 25 | 27 | 29 | 31 |
| mAb26049 | 33 | 35 | 37 | 39 | 41 | 43 | 45 | 47 |
| mAb26076 | 49 | 51 | 53 | 55 | 57 | 59 | 61 | 63 |

Antibodies referred to herein typically have fully human variable regions, but may have human or mouse constant regions. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 2—will remain the same, and the binding properties to antigen are expected to be identical or substantially similar regardless of the nature of the Fc domain. In certain embodiments, selected antibodies with a mouse IgG1 Fc are converted to antibodies with human IgG4 Fc. In one embodiment, the IgG4 Fc domain comprises 2 or more amino acid changes as disclosed in US20100331527. In one embodiment, the human IgG4 Fc comprises a serine to proline mutation in the hinge region (S108P) to promote dimer stabilization.

Control Constructs Used in the Following Examples

The following control constructs (anti-FXII antibodies) were included in the experiments disclosed herein, for comparative purposes: "Comparator 1," a monoclonal antibody against human FXII/FXIIa having $V_H/V_L$ sequences of antibody "3F7" according to U.S. Pat. No. 9,518,127 (CSL Behring GmbH); and "Comparator 2," a human monoclonal antibody against human FXII having $V_H/V_L$ sequences of antibody "15H8" according to U.S. Pat. No. 9,574,013 (Vanderbilt Univ./Aronora).

Example 3: Antibody Binding to FXII as Determined by Surface Plasmon Resonance Equilibrium dissociation constant ($K_D$) for different FXII reagents binding to purified anti-FXII monoclonal antibodies were determined using a real-time surface plasmon resonance based Biacore 4000 biosensor. All binding studies were performed in 10 mM HEPES, 300 mM NaCl, and 0.05% v/v Surfactant Tween-20, pH 7.4 (HBS-P) running buffer at 25° C. and 37° C. The Biacore CM5 sensor chip surface was first derivatized by amine coupling with the mouse anti-human Fc specific monoclonal antibody (GE Healthcare Cat #BR100839) to capture anti-FXII monoclonal antibodies. Binding studies were performed on human FXII and FXIIa (Enzyme Research Laboratories, Cat #1212 and 1212a, respectively). Different concentrations of hFXII and hFXIIa (50 nM-3.125 nM; 2-fold serial dilution) were first prepared in HBS-P running buffer and were injected over anti-human Fc captured anti-FXII monoclonal antibody surface for 3 minutes at a flow rate of 30 uL/minute, while the dissociation of monoclonal antibody bound FXII reagent was monitored for 5 minutes in HBS-P running buffer. The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life ($t\frac{1}{2}$) were calculated from the kinetic rates as:

$$K_D(M) = \frac{kd}{ka}, \text{ and } t^{1/2}(\min) = \frac{\ln(2)}{60 * kd}$$

Binding kinetics parameters for hFXII or hFXIIa binding to different anti-FXII monoclonal antibodies of the invention at 25° C. and 37° C. are shown in Tables 3 through 6.

TABLE 3

Binding kinetics parameters of hFXII binding to selected antibodies at 25° C.

| mAb Captured | mAb Capture Level (RU) | 100 nM Ag Bound (RU) | $k_a$ (1/Ms) | $k_d$ (1/s) | KD (M) | t½ (min) |
| --- | --- | --- | --- | --- | --- | --- |
| mAb26036 | 469.1 ± 0.1 | 146.2 | 7.63E+04 | 2.38E−04 | 3.12E−09 | 48.5 |
| mAb26048 | 415.3 ± 0.8 | 327.5 | 3.61E+05 | 3.17E−04 | 8.79E−10 | 36.5 |
| mAb26049 | 348.4 ± 0.7 | 134.6 | 9.01E+04 | 2.47E−04 | 2.74E−09 | 46.7 |
| mAb26076 | 328.9 ± 0.6 | 242.7 | 4.85E+05 | 1.50E−03 | 3.10E−09 | 7.7 |
| Comparator 1 | 534.7 ± 1.0 | 9.5 | NB | NB | NB | NB |
| Comparator 2 | 634.7 ± 0.7 | 86.1 | 6.61E+04 | 2.47E−03 | 3.73E−08 | 4.7 |
| Isotype control | 683.9 ± 347 | 10 | NB | NB | NB | NB |

TABLE 4

Binding kinetics parameters of hFXII binding to selected antibodies at 37° C.

| mAb Captured | mAb Capture Level (RU) | 100 nM Ag Bound (RU) | $k_a$ (1/Ms) | $k_d$ (1/s) | KD (M) | t½ (min) |
| --- | --- | --- | --- | --- | --- | --- |
| mAb26036 | 637.4 ± 1.8 | 272.3 | 1.21E+05 | 5.60E−04 | 4.62E−09 | 20.6 |
| mAb26048 | 562.9 ± 0.2 | 400.6 | 2.76E+05 | 6.98E−04 | 2.53E−09 | 17 |
| mAb26049 | 497.5 ± 1.0 | 178.5 | 8.70E+04 | 7.64E−04 | 8.78E−09 | 15 |
| mAb26076 | 471.8 ± 1.5 | 258.9 | 4.00E+05 | 6.74E−03 | 1.68E−08 | 2 |
| Comparator 1 | 724.8 ± 4.2 | 9.9 | NB | NB | NB | NB |
| Comparator 2 | 766.6 ± 0.8 | 83.8 | 1.20E+06 | 5.42E−02 | 4.53E−08 | 0 |
| Isotype control | 823.9 ± 1.5 | 10.3 | NB | NB | NB | NB |

TABLE 5

Binding kinetics parameters of hFXIIa binding to selected antibodies at 25° C.

| mAb Captured | mAb Capture Level (RU) | 100 nM Ag Bound (RU) | $k_a$ (1/Ms) | $k_d$ (1/s) | KD (M) | t½ (min) |
| --- | --- | --- | --- | --- | --- | --- |
| mAb26036 | 471.6 ± 2.9 | 89.9 | 4.28E+04 | 1.62E−04 | 3.78E−09 | 71.4 |
| mAb26048 | 414.0 ± 1.3 | 267.8 | 2.08E+05 | 4.30E−04 | 2.07E−09 | 26.8 |
| mAb26049 | 345.5 ± 1.3 | 162.4 | 9.76E+04 | 4.95E−04 | 5.07E−09 | 23.4 |
| mAb26076 | 326.5 ± 1.4 | 221 | 6.34E+05 | 3.84E−04 | 6.06E−10 | 30.1 |
| Comparator 1 | 534.5 ± 1.6 | 297.1 | 3.92E+05 | 9.96E−04 | 2.54E−09 | 11.6 |
| Comparator 2 | 631.3 ± 1.8 | 196.7 | 1.54E+06 | 4.51E−03 | 2.93E−09 | 2.6 |
| Isotype control | 677.9 ± 0.6 | 0.1 | NB | NB | NB | NB |

TABLE 6

Binding kinetics parameters of hFXIIa binding to selected antibodies at 37° C.

| mAb Captured | mAb Capture Level (RU) | 100 nM Ag Bound (RU) | $k_a$ (1/Ms) | $k_d$ (1/s) | KD (M) | t½ (min) |
| --- | --- | --- | --- | --- | --- | --- |
| mAb26036 | 634.3 ± 0.8 | 166.52 | 8.46E+04 | 4.01E−04 | 4.74E−09 | 29 |
| mAb26048 | 561.4 ± 1.0 | 335.6 | 4.39E+05 | 7.84E−04 | 1.79E−09 | 15 |
| mAb26049 | 491.4 ± 2.8 | 251.5 | 2.44E+05 | 1.54E−03 | 6.31E−09 | 7 |
| mAb26076 | 468.4 ± 1.3 | 280.2 | 1.02E+06 | 1.84E−03 | 1.80E−09 | 6 |
| Comparator 1 | 720.8 ± 1.6 | 311.6 | 6.24E+05 | 5.15E−03 | 8.25E−09 | 2 |
| Comparator 2 | 762.0 ± 1.6 | 186.8 | 7.25E+06 | 2.00E−02 | 2.76E−09 | 1 |
| Isotype control | 816.5 ± 2.8 | −2.7 | NB | NB | NB | NB |

At 25° C., the antibodies bound to hFXII with KD values ranging from 0.88 nM to 3.12 nM, as shown in Table 3. At 37° C., the antibodies bound to hFXII with KD values ranging from 2.53 nM to 16.8 nM, as shown in Table 4.

At 25° C., the antibodies bound to hFXIIa with KD values ranging from 0.61 nM to 5.07 nM, as shown in Table 5. At 37° C., the antibodies bound to hFXIIa with KD values ranging from 1.79 nM to 8.25 nM, as shown in Table 6.

Example 4: Octet Cross-Competition Assay

Binding competition between anti-FXII monoclonal antibodies was determined using a real time, label-free bio-layer interferometry assay on an OctetHTX biosensor (Pall ForteBio Corp.). The entire experiment was performed at 25° C. in 0.01 M HEPES pH7.4, 0.15M NaCl, 0.05% v/v Surfactant Tween-20, 0.1 mg/mL BSA (Octet HBS-P buffer) with the plate shaking at the speed of 1000 rpm. To assess whether 2 antibodies were able to compete with one another for binding to their respective epitopes on a human FXII (ERL) around 0.42-0.53 nm of anti-human FXII monoclonal antibody was first captured onto anti-hFc antibody coated Octet biosensor tips (Pall ForteBio Corp., #18-5060) by submerging the tips for 3 minutes into wells containing a 50 μg/mL solution of anti-human FXII monoclonal antibody (subsequently referred to as mAb-1). The antibody captured biosensor tips were then saturated with a blocking mAb isotype control monoclonal antibody (subsequently referred to as blocking mAb) by dipping into wells containing 200 μg/mL solution of blocking mAb for 4 minutes. The biosensor tips were then subsequently dipped into wells containing a co-complexed solution of 25 nM hFXII and 1 μM of a second anti-human FXII monoclonal antibody (subsequently referred to as mAb-2), that had been pre-incubated for 2 hours. The biosensor tips were washed in Octet HBS-P buffer in between every step of the experiment. The real-time binding response was monitored during the course of the experiment and the binding response at the end of every step was recorded. The response of human FXII pre-complexed mAb-2 binding to mAb-1 was corrected for background binding, compared and competitive/non-competitive behavior of different anti-FXII monoclonal antibodies was determined.

TABLE 7

Cross-competition of anti-hFXII/FXIIa antibodies for binding to human FXII

| First mAb (mAb-1) Captured using AHC Octet Biosensors | mAb-2 Antibodies Shown to Compete with mAb-1 |
|---|---|
| mAb26036 | mAb26048 |
|  | mAb26076 |
| mAb26048 | mAb26036 |
|  | mAb26076 |
|  | mAb26049 |
| mAb26076 | mAb26036 |
|  | mAb26048 |
|  | mAb26049 |
| mAb26049 | mAb26048 |
|  | mAb26076 |

Table 7 explicitly defines the relationships of antibodies competing in both directions, independent of the order of binding.

Example 5: Functional Plasma Assays to Determine the Inhibitory Activity of Anti-FXII/FXIIa Antibodies This Example describes the inhibitory activity of selected antibodies, as determined by four functional plasma assays: 1) Activated Partial Thromboplastin Time (aPTT), 2) Prothrombin Time (PT), 3) Thrombin Generation Assay (TGA) triggered by ellagic acid and 4) TGA triggered by Tissue Factor. The aPTT test evaluates all clotting factors of the Intrinsic and Common pathways of the coagulation cascade by measuring time for a clot to form after the addition of calcium and ellagic acid, whereas the PT test evaluates all clotting factors of the Extrinsic and Common pathways of the coagulation cascade after the addition of calcium and Tissue Factor. The TGA triggered by ellagic acid measures the rate and amount of thrombin generated via the Intrinsic and Common pathways whereas TGA triggered by Tissue Factor measures the rate and amount of thrombin generated via the Extrinsic and Common pathways.

Determination of aPTT

The aPTT was determined on Diagnostica Stago STart4 Hemostasis Analyzer in the following manner: A total of 50 ul of pooled normal human plasma was added to a cuvette at 37° C. After 1 min, 5 ul of a 2× serially diluted test article (antibody or small molecule inhibitor) in PBS was added to the cuvette and allowed to incubate for 5 min. Then 50 ul of APPT-XL Ellagic Acid (Thermo Scientific) was added and allowed to incubate for 300 seconds before 50 ul of 20 mM calcium chloride (Thermo Scientific) was added to start the reaction. The measured clot time for the test article concentration was normalized to baseline (no drug) plasma clot time and plotted against log molar concentration of the test article. The results were analyzed using nonlinear regression (4-parameter logistics) with Prism 5 software (GraphPad) to obtain doubling time concentration.

Determination of PT

The PT was determined on Diagnostica Stago STart4 Hemostasis Analyzer in the following manner. A total of 50 ul of pooled normal human plasma was added to a cuvette at 37° C. After 1 min, 5 ul of a 2× serially diluted test article (antibody or small molecule inhibitor) in PBS was added to the cuvette and allowed to incubate for 5 min. Then 100 ul of Tissue Factor (TriniCLOT PT Excel, Diagnostica Stago) was added to start the reaction. The measured clot time for the test article concentration was normalized to baseline (no drug) plasma clot time and plotted against log molar concentration of the test article. The results were analyzed using nonlinear regression (4-parameter logistics) with Prism 5 software (GraphPad) to obtain doubling time concentration.

Determination of TGA with Ellagic Acid

The thrombin generation profile was determined in a Thermo Scientific Hemker Thrombinoscope in the following manner: A total of 55 ul of pooled normal human plasma was added to a well of a microplate at 37° C. Then 5 ul of a 2× serially diluted test article (antibody or small molecule inhibitor) in PBS was added to the well of the microplate and allowed to incubate for 30 min. 15 ul of APPT-XL Ellagic Acid (Thermo Scientific) was diluted in MP reagent then added to the well and allowed to incubate for 45 min. Then 15 ul of Fluo Flu Cal substrate (Diagnostica Stago) was added immediately before a continuous 90 min reading of the microplate. The measured real-time thrombin concentration values were plotted against time to yield a thrombogram profile for each concentration of the test article used.

Determination of TGA with Tissue Factor

The thrombin generation profile was determined in a Thermo Scientific Hemker Thrombinoscope in the following manner: A total of 55 ul of pooled normal human plasma was added to a well of a microplate at 37° C. Then 5 ul of a 2× serially diluted test article (antibody or small molecule inhibitor) in PBS was added to the well of the microplate and allowed to incubate for 30 min. 15 ul of Tissue Factor PPP Reagent (Diagnostica Stago) was added to the well and allowed to incubate for 45 min. Then 15 ul of Fluo Flu Cal substrate (Diagnostica Stago) was added immediately before a continuous 90 min reading of the microplate. The measured real-time thrombin concentration values were plotted against time to yield a thrombogram profile for each concentration of the test article used.

Results

Dose response curves were generated to determine the effect of each drug on plasma aPTT and PT. The IgG4 isotype control antibody exerted no effect on aPTT or PT. The anti-FXII/FXIIa antibodies (mAb26036, mAb26048, mAb26049 and mAb26076) prolonged the aPTT without increasing PT. The clinically approved anticoagulant FXa inhibitor, Apixaban prolonged both aPTT and PT with uM concentrations. Comparator 1 prolonged the aPTT without increasing PT. The efficiency of the drug to inhibit coagulation activity is indexed by an arbitrary "doubling time" concentration or $C_{2xt}$, which is the concentration of drug required to prolong the clotting time by two-fold over the baseline value. These extrapolated $C_{2xt}$ values (i.e., curves cross the "Doubling Time Line") for the drugs are listed in Table 8.

TABLE 8

Concentration of drug required to increase clotting time by 2-fold over baseline

| | $C_{2xt}$ of activated Partial Thromboplastin Time (aPTT) - Intrinsic Pathway | $C_{2xt}$ of Prothrombin Time (PT) - Extrinsic Pathway |
|---|---|---|
| Apixaban | 7 uM | 3.5 uM |
| Isotype control | — | — |
| Comparator 1 | 250 nM | — |
| mAb26036 | 175 nM | — |
| mAb26048 | 150 nM | — |
| mAb26049 | 200 nM | — |
| mAb26076 | 250 nM | — |

$C_{2xt}$ = Conc. of drug required to increase clotting time by 2-fold over baseline
(—) = no inhibitory effect on clotting time with a dose up to 4 uM The antibodies mAb26036, mAb26048 and mAb26049 reached a $C_{2xt}$ with ≤200 nM whereas the mAb26076 required 250 nM. All antibodies were not found to double the PT clotting time at the maximal 4 uM tested. Apixaban reached a aPTT $C_{2xt}$ with 7 uM, which was greater than the concentration of 3.5 uM needed to achieve a PT $C_{2xt}$. Comparator 1 required 250 nM to reach a aPTT $C_{2xt}$ but did not reach a PT $C_{2xt}$ with 4 uM.

The antibodies were evaluated for their ability to inhibit thrombin generation (i.e., prolonged time to detection of thrombin=lag time, reduction in thrombin peak and reduction in total amount of thrombin generated=endogenous thrombin potential) when plasma was triggered by ellagic acid or Tissue Factor. The isotype control had no effect on thrombin generation. The antibodies showed a slight reduction in thrombin generation at 125 nM but significantly or completely inhibited thrombin production at concentrations ≥250 nM, indicating that the antibodies suppress the Intrinsic pathway activation that in turn prevents thrombin generation. Apixaban showed a dose dependent reduction in thrombin generation but was not able to reach the 2× lag time or ½ the ETP or peak at the highest dose (500 nM) used. Comparator 1 showed a dose dependent effect on thrombin generation with a near complete inhibition at 500 nM. Thrombin generation triggered by Tissue Factor was not affected by the control isotype antibody. The antibodies did not inhibit thrombin generation triggered by Tissue Factor. Apixaban dose dependently inhibited thrombin generation when triggered by Tissue Factor. Comparator 1 had no effect on thrombin generation triggered by Tissue Factor. The concentrations of test article required to extend the lag time by two-fold, reduce the thrombin peak and total amount of thrombin generation by half when coagulation is activated by ellagic acid or Tissue Factor are summarized in Table 9.

TABLE 9

Concentration of drug required to delay and reduce thrombin generation

| | Intrinsic Pathway Activation with Ellagic Acid | | | Extrinsic Pathway Activation with Tissue Factor | | |
|---|---|---|---|---|---|---|
| | ↑ lag time by 2× | ↓ endogenous thrombin potential by ½ | ↓ thrombin peak by ½ | ↑ lag time by 2× | ↓ endogenous thrombin potential by ½ | ↓ thrombin peak by ½ |
| Apixaban | — | — | — | 250 nM | 250 nM | 62.5 nM |
| Isotype control | — | — | — | — | — | — |
| Comparator 1 | 250 nM | 125 nM | 250 nM | — | — | — |
| mAb26036 | 175 nM | 250 nM | 250 nM | — | — | — |
| mAb26048 | 150 nM | 250 nM | 250 nM | — | — | — |
| mAb26049 | 200 nM | 250 nM | 250 nM | — | — | — |
| mAb26076 | 250 nM | 250 nM | 250 nM | — | — | — |

(—) = no effect on thrombin generation with a dose up to 500 nM

The above results show that the exemplified antibodies inhibit thrombin generation by intrinsic pathway without inhibiting the extrinsic pathway.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An antibody, of antigen-binding fragment thereof, that binds specifically to Factor XII (FXII), wherein the antibody, or antigen-binding fragment thereof, has one or more of the following characteristics:
   (a) is a fully human monoclonal antibody;
   (b) binds to activated Factor XII (FXIIa);
   (c) binds to FXII with a dissociation constant ($K_D$) of less than 3.5 nM at 25° C., as measured in a surface plasmon resonance assay;
   (d) binds to FXII with a $K_D$ of less than 17 nM at 37° C., as measured in a surface plasmon resonance assay;
   (e) binds to FXIIa with a $K_D$ of less than 5 nM, preferably less than 2.5 nM, at 25° C. as measured in a surface plasmon resonance assay;
   (f) binds to FXIIa with a $K_D$ of less than 6.5 nM, preferably less than 2.5 nM, at 37° C. as measured in a surface plasmon resonance assay;
   (g) blocks thrombin generation by intrinsic pathway at a concentration of less than 250 nM, as measured by functional plasma assays; and
   (h) blocks thrombin generation by intrinsic pathway without blocking thrombin generation by extrinsic pathway, as measured by functional plasma assays.

2. The antibody, or antigen-binding fragment thereof, of claim 1, wherein the antibody, or antigen-binding fragment thereof, comprises three heavy chain complementarity determining regions (CDRs) (HCDR1, HCDR2 and HCDR3) contained within a heavy chain variable region (HCVR); and three light chain CDRs (LCDR1, LCDR2 and LCDR3) contained within a light chain variable region (LCVR), wherein the HCVR has an amino acid sequence selected from the group consisting of HCVR sequences listed in Table 1.

3. The antibody, or antigen-binding fragment thereof, of claim 2, comprising a LCVR having an amino acid sequence selected from the group consisting of LCVR sequences listed in Table 1.

4. The antibody, or antigen-binding fragment thereof, of claim 2 comprising:
   (a) a HCDR1 domain having an amino acid sequence selected from the group consisting of SEQ ID NOs: 4, 20, 36, and 52;
   (b) a HCDR2 domain having an amino acid sequence selected from the group consisting of SEQ ID NOs: 6, 22, 38, and 54;
   (c) a HCDR3 domain having an amino acid sequence selected from the group consisting of SEQ ID NOs: 8, 24, 40, and 56;
   (d) a LCDR1 domain having an amino acid sequence selected from the group consisting of SEQ ID NOs: 12, 28, 44, and 60;
   (e) a LCDR2 domain having an amino acid sequence selected from the group consisting of SEQ ID NOs: 14, 30, 46, and 62; and
   (f) a LCDR3 domain having an amino acid sequence selected from the group consisting of SEQ ID NOs: 16, 32, 48, and 64.

5. The antibody, or antigen-binding fragment thereof, of claim 4, comprising CDRs selected from the group consisting of: (a) SEQ ID NOs: 4, 6, 8, 12, 14, and 16; (b) SEQ ID NOs: 20, 22, 24, 28, 30 and 32; (c) SEQ ID NOs: 36, 38, 40, 44, 46 and 48; and (d) SEQ ID NOs: 52, 54, 56, 60, 62 and 64.

6. The antibody, or antigen-binding fragment thereof, of claim 5, comprising a HCVR/LCVR amino acid sequence pair selected from the group consisting of SEQ ID NOs: 2/10, 18/26, 34/42, and 50/58.

7. An antibody, or antigen-binding fragment thereof, that binds to FXII/FXIIa, wherein the antibody, or antigen-binding fragment thereof, comprises three heavy chain CDRs (HCDR1, HCDR2 and HCDR3) contained within a HCVR and three light chain CDRs (LCDR1, LCDR2 and LCDR3) contained within a LCVR; wherein the HCVR comprises:
   (i) an amino acid sequence selected from the group consisting of SEQ ID NOs: 2, 18, 34, and 50,
   (ii) an amino acid sequence having at least 90% identity to the amino acid sequence selected from the group consisting of SEQ ID NOs: 2, 18, 34, and 50,
   (iii) an amino acid sequence having at least 95% identity to the amino acid sequence selected from the group consisting of SEQ ID NOs: 2, 18, 34, and 50; or
   (iv) an amino acid sequence selected from the group consisting of SEQ ID NOs: 2, 18, 34, and 50 having no more than 12 amino acid substitutions;
   and the LCVR comprises:
   (i) an amino acid sequence selected from the group consisting of SEQ ID NOs: 10, 26, 42, and 58,
   (ii) an amino acid sequence having at least 90% identity to the amino acid sequence selected from the group consisting of SEQ ID NOs: 10, 26, 42, and 58,
   (iii) an amino acid sequence having at least 95% identity to the amino acid sequence selected from the group consisting of SEQ ID NOs: 10, 26, 42, and 58; or
   (iv) an amino acid sequence selected from the group consisting of SEQ ID NOs: 10, 26, 42, and 58 having no more than 10 amino acid substitutions.

8. The antibody, or antigen-binding fragment thereof, of claim 7, comprising a HCVR having an amino acid sequence selected from the group consisting of SEQ ID NOs: 2, 18, 34, and 50.

9. The antibody, or antigen-binding fragment thereof, of claim 7, comprising a LCVR having an amino acid sequence selected from the group consisting of SEQ ID NOs: 10, 26, 42, and 58.

10. The antibody, or antigen-binding fragment thereof, of claim 7, comprising three CDRs contained within a HCVR selected from the group consisting of SEQ ID NOs: 2, 18, 34, and 50; and three CDRs contained within a LCVR selected from the group consisting of SEQ ID NOs: 10, 26, 42 and 58.

11. The antibody, or antigen-binding fragment thereof, of claim 7, comprising a HCVR/LCVR amino acid sequence pair selected from the group consisting of SEQ ID NOs: 2/10, 18/26, 34/42, and 50/58.

12. The antibody, or antigen-binding fragment thereof, of claim 7, comprising:
   (a) a HCDR1 domain having an amino acid sequence selected from the group consisting of SEQ ID NOs: 4, 20, 36, and 52;

(b) a HCDR2 domain having an amino acid sequence selected from the group consisting of SEQ ID NOs: 6, 22, 38, and 54;

(c) a HCDR3 domain having an amino acid sequence selected from the group consisting of SEQ ID NOs: 8, 24, 40, and 56;

(d) a LCDR1 domain having an amino acid sequence selected from the group consisting of SEQ ID NOs: 12, 28, 44, and 60;

(e) a LCDR2 domain having an amino acid sequence selected from the group consisting of SEQ ID NOs: 14, 30, 46, and 62; and (f) a LCDR3 domain having an amino acid sequence selected from the group consisting of SEQ ID NOs: 16, 32, 48, and 64.

13. The antibody, or antigen-binding fragment thereof, of claim 12, comprising CDRs selected from the group consisting of: (a) SEQ ID NOs: 4, 6, 8, 12, 14, and 16; (b) SEQ ID NOs: 20, 22, 24, 28, 30 and 32; (c) SEQ ID NOs: 36, 38, 40, 44, 46 and 48; and (d) SEQ ID NOs: 52, 54, 56, 60, 62 and 64.

14. The antibody, or antigen-binding fragment thereof, of claim 13, comprising a HCVR having an amino acid sequence selected from the group consisting of SEQ ID NOs: 2, 18, 34, and 50.

15. The antibody, or antigen-binding fragment thereof, of claim 13, comprising a LCVR having an amino acid sequence selected from the group consisting of SEQ ID NOs: 10, 26, 42, and 58.

16. The antibody, or antigen-binding fragment thereof, of claim 12, comprising a HCVR/LCVR amino acid sequence pair selected from the group consisting of SEQ ID NOs: 2/10, 18/26, 34/42, and 50/58.

17. An antibody, or antigen-binding fragment thereof, that competes for binding to Factor XII with an antibody, or antigen-binding fragment thereof, of claim 1 or 7.

18. An antibody, or antigen-binding fragment thereof, that binds to the same epitope as an antibody, or antigen-binding fragment thereof, of claim 1 or 7.

19. A pharmaceutical composition comprising the isolated antibody, or antigen-binding fragment thereof, that binds to Factor XII/XIIa according to claim 1 and a pharmaceutically acceptable carrier or diluent.

20. An isolated polynucleotide molecule comprising a polynucleotide sequence that encodes a HCVR of an antibody, or antigen-binding fragment thereof, as set forth in claim 1.

21. An isolated polynucleotide molecule comprising a polynucleotide sequence that encodes a LCVR of an antibody, or antigen-binding fragment thereof, as set forth in claim 1.

22. A vector comprising the polynucleotide sequence of claim 20 or 21.

23. A cell expressing the vector of claim 22.

24. A method of producing an anti-FXII/FXIIa antibody or antigen-binding fragment thereof, comprising growing the host cell of claim 23 under conditions permitting production of the antibody or fragment, and recovering the antibody or fragment so produced.

25. The method of claim 24, further comprising formulating the antibody or antigen-binding fragment thereof as a pharmaceutical composition comprising an acceptable carrier.

26. A method of preventing the formation of a thrombus or treating a subject at risk of thrombus formation, the method comprising administering a pharmaceutical composition comprising a therapeutically effective amount of the antibody, or antigen-binding fragment thereof, of claim 1 to a subject in need thereof, thereby preventing the formation of the thrombus or treating the subject at risk of thrombus formation.

27. The method of claim 26, wherein the subject has a disease, disorder or condition selected from the group consisting of venous thrombosis, arterial thrombosis, device thrombosis, thromboembolism, hereditary angioedema, stroke, thrombophilia, cardiac ischemia, atherosclerotic plaque rupture, use of mechanical valve prostheses, use of blood-contacting medical devices, use of blood-contacting extracorporeal circuits, venous thromboembolism, pulmonary embolism, deep vein thrombosis, portal vein thrombosis, Budd-Chiari syndrome, Paget-Schroetter disease, renal vein thrombosis, cerebral venous sinus thrombosis, jugular vein thrombosis, cavernous sinus thrombosis, hepatic artery thrombosis, limb ischemia and myocardial infarction.

28. The method of claim 26 or 27, wherein the pharmaceutical composition is administered prophylactically or therapeutically to the subject.

29. The method of claim 26, wherein the pharmaceutical composition is administered in combination with a second therapeutic agent.

30. The method of claim 29, wherein the second therapeutic agent is selected from the group consisting of an anti-coagulant, a direct thrombin inhibitor, a thrombolytic drug, a fibrinolytic drug, an anti-platelet drug, an anti-inflammatory drug, an anti-hypertensive drug, a second anti-FXII antibody, a lipid-lowering drug, mechanical clot retrieval, catheter-guided thrombolysis, compression stockings, and surgery.

31. The method of claim 26, wherein the pharmaceutical composition is administered to the subject subcutaneously, intravenously, intradermally, intraperitoneally, or intramuscularly.

* * * * *